United States Patent [19]

Passafiume

[11] 4,279,369
[45] Jul. 21, 1981

[54] METHOD AND APPARATUS FOR PARTITIONING AND SHAPING A FIBROUS BATT

[75] Inventor: Anthony Passafiume, Burbank, Ill.

[73] Assignee: Johnson & Johnson Baby Products Company, New Brunswick, N.J.

[21] Appl. No.: 51,562

[22] Filed: Jun. 25, 1979

[51] Int. Cl.³ .............................................. B26F 3/02
[52] U.S. Cl. ....................................... 225/3; 83/117; 83/348; 225/4; 225/101; 225/106
[58] Field of Search ...................... 83/348, 117; 225/1, 225/3, 4, 101, 106

[56] References Cited

U.S. PATENT DOCUMENTS

| 1,814,867 | 7/1931 | Swift, Jr. ................................ 83/117 |
| 1,937,519 | 12/1933 | Lamatsch ........................... 83/117 X |
| 2,172,359 | 9/1939 | Campbell ............................ 83/348 X |
| 3,133,684 | 5/1964 | Wiltshire et al. ..................... 225/101 |
| 3,433,107 | 3/1969 | Horton et al. ...................... 83/348 X |
| 3,807,262 | 4/1974 | Vits ...................................... 83/117 |
| 3,957,186 | 5/1976 | Babcock .......................... 225/101 X |

Primary Examiner—Frank T. Yost

[57] ABSTRACT

Method and apparatus for partitioning and/or shaping a fibrous batt by gripping the batt along adjacent lines with resilient means gripping one surface and non-resilient means gripping the opposite surface and displacing said lines with respect to each other to separate the batt without compacting the parted edges of the batt.

31 Claims, 6 Drawing Figures

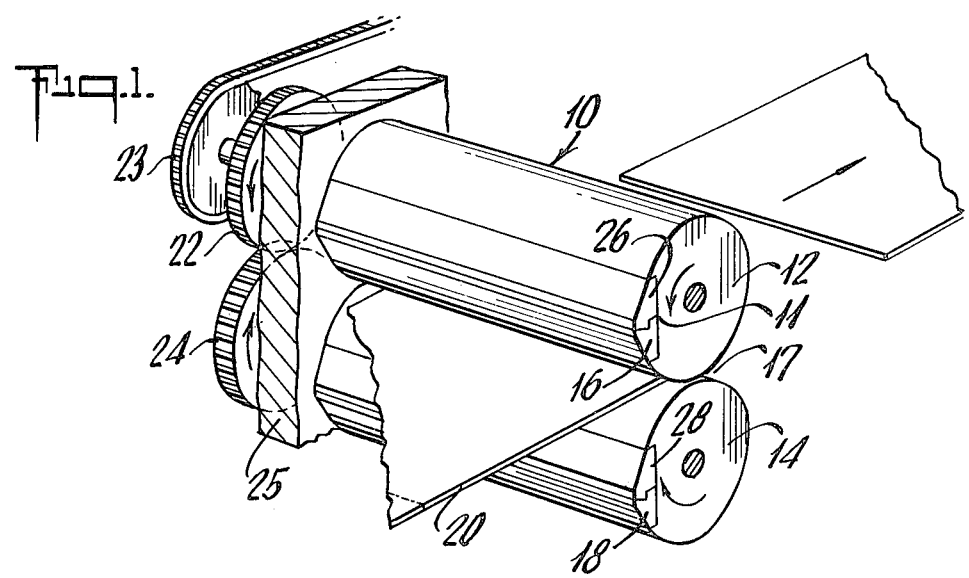
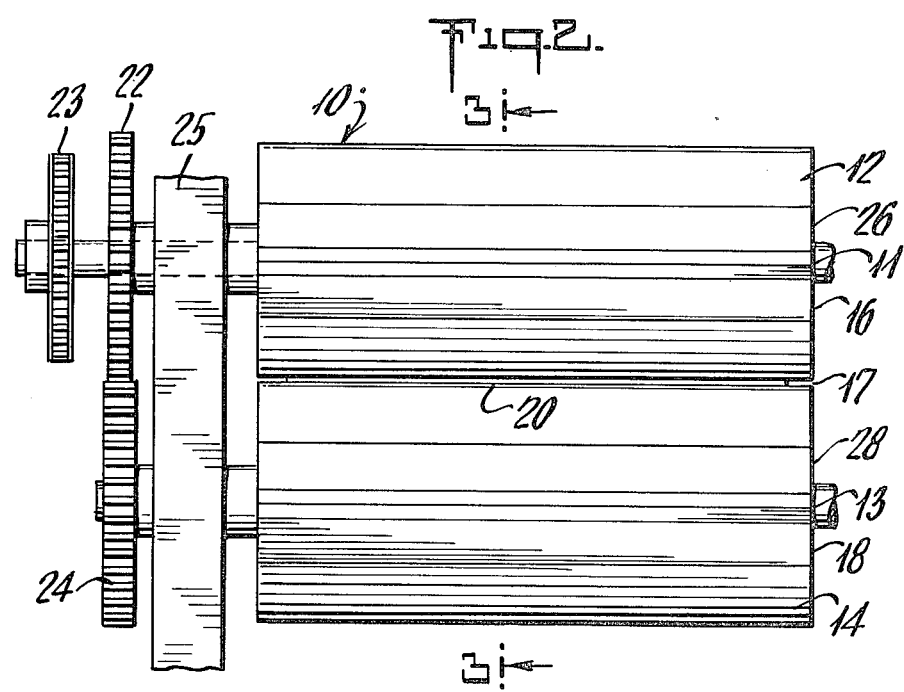

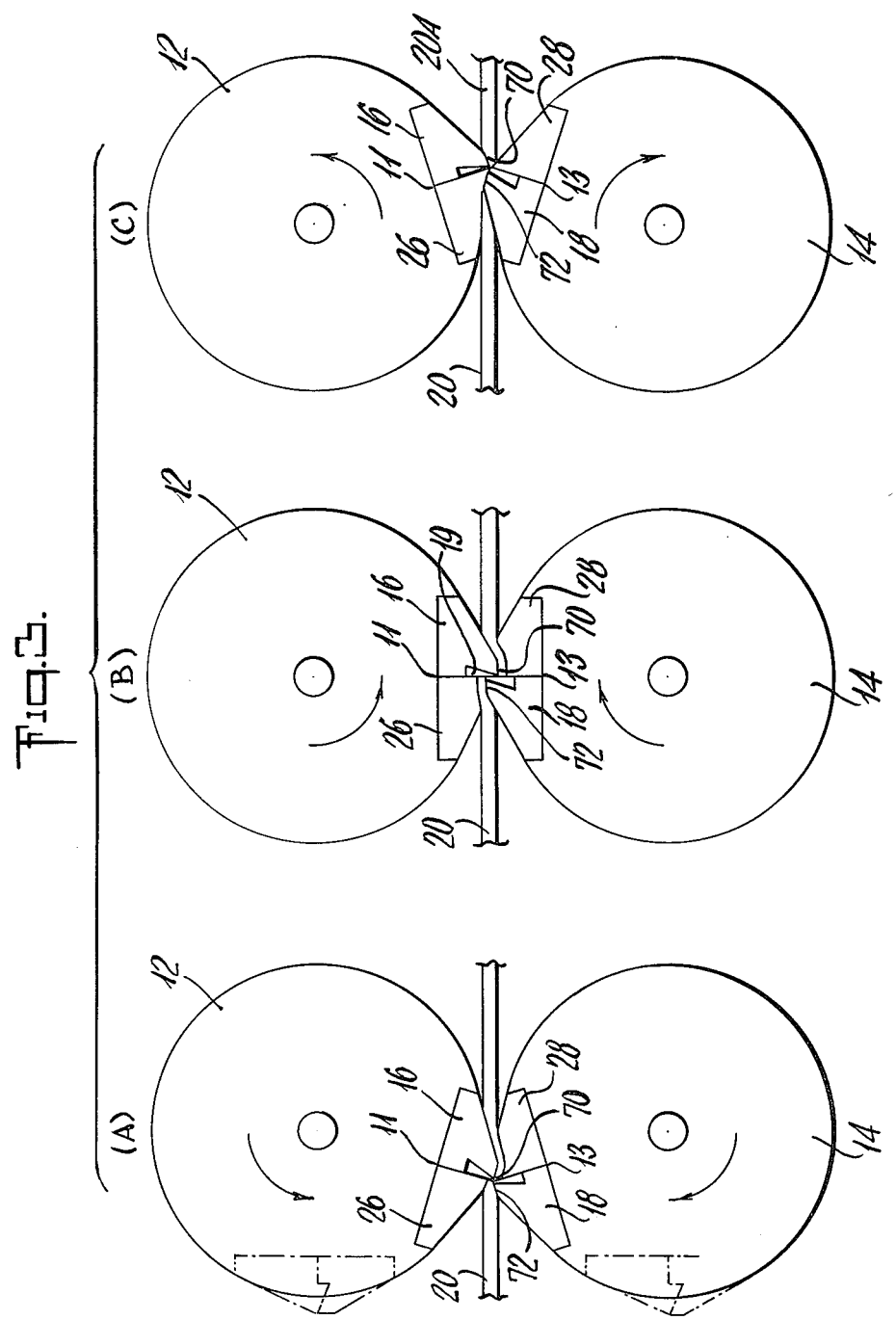

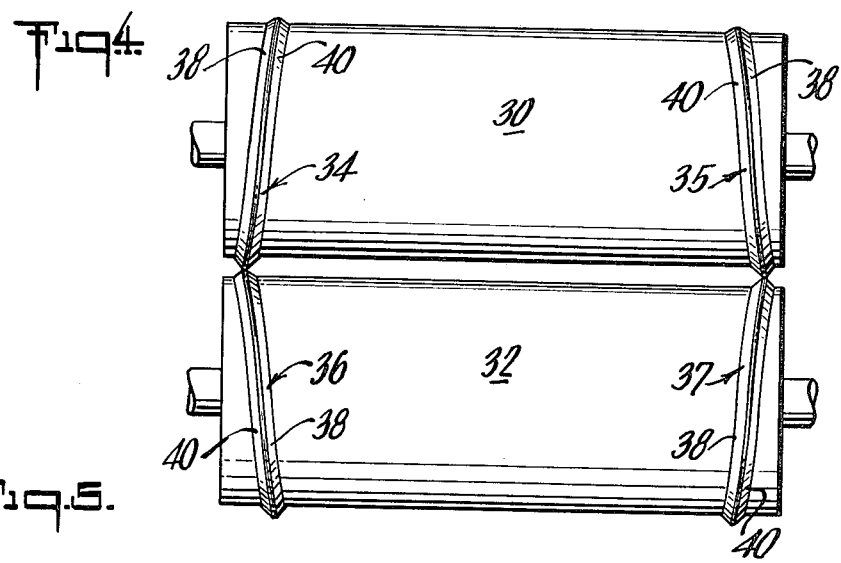
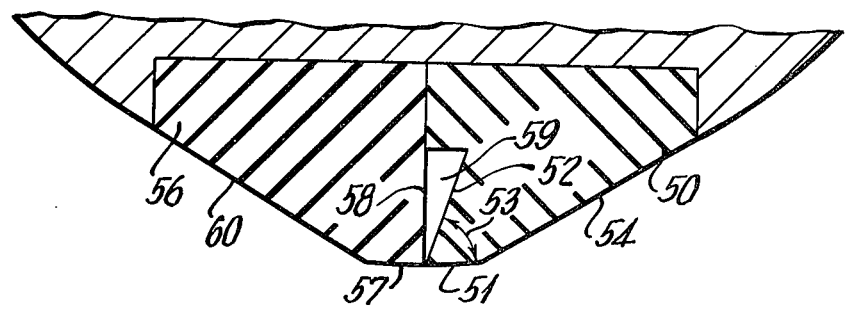
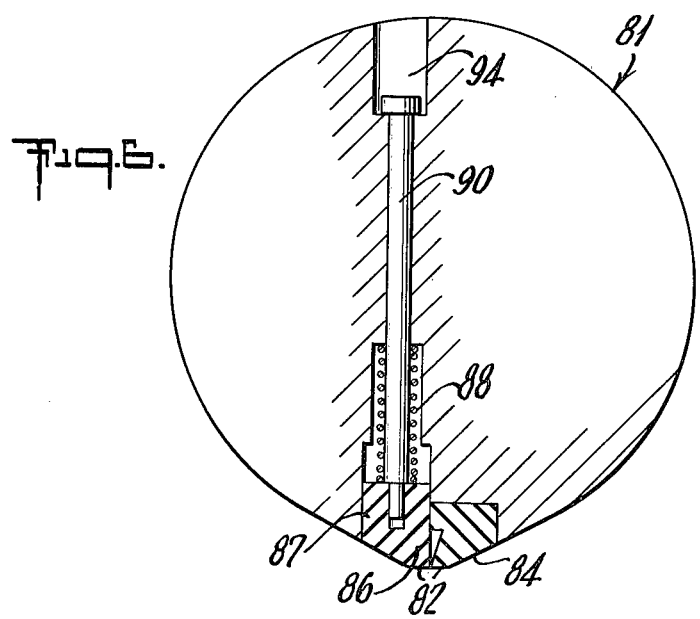

METHOD AND APPARATUS FOR PARTITIONING AND SHAPING A FIBROUS BATT

BACKGROUND OF THE INVENTION

Many absorbent products, such as disposable diapers, sanitary napkins, and the like, include an absorbent panel. The absorbent panel is formed of loosely compacted short fibers, such as wood pulp fibers or cotton linters, or mixtures thereof, and the like. The panel is produced by taking a source of short fibers such as a pulp board and grinding the board and individualizing the fibers therein using a grinding mill. The individualized fibers are collected on a screen or other permeable means in the form of a layer or batt of loosely associated short fibers. The batt is usually lightly compacted to provide some integrity.

In some absorbent products, a panel of a specific size may be desired while in other absorbent products a panel of a specific size and shape may be desired. In the past, it has been the usual practice to sever sections from an absorbent batt by cutting the batt, as with a knife or scissors. Due to the loose structure of the fibers in such batts, this type of severance often results in permanent compression of the fibers at the severance line. As a result of this compression, the density of the fibers in this region is greatly increased and, consequently, the wickability or preferential absorptivity along the line of permanent compression is greatly increased. This result may be most disadvantageous in the formation of a diaper panel since urine will migrate along a line of densification that comes into contact with it. If this densification line occurs at an edge, as where the panel section has been cut with a knife edge, there is a strong tendency for any liquid coming into contact with the line to be drawn into and concentrated at the line, resulting in premature leakage of urine from the diaper structure. Furthermore, the above method of cutting the batt results in harshness of the batt at the compressed line.

Since the structure of absorbent batts is loose, these batts may be quite easily torn when stressed. Moreover, if the tearing can be done without compressing the fibers of the batt, no densification lines will be created at the edge. U.S. Pat. Nos. 3,895,751 and 3,957,186 disclose devices which tear a batt to form panels without creating densification at the tear line. The first-mentioned patent discloses an apparatus for tearing an intermittently fed batt wherein a pair of juxtaposed opposing jaws operate transversely on a batt to form panels. Each pair of jaws consists of a first jaw and a second biased hinged jaw, so that after the jaws grip the batt, the first jaw holds the batt and the second jaw is displaced from its juxtaposed position, thus tearing the batt transversely. The apparatus of the second patent consists of two opposed, rotatable pairs of batt-engaging cylinders comprising a trailing jaw member and a juxtaposed leading jaw member. The cylinders are simultaneously rotating in opposite directions. As the batt is engaged by the jaws, a displacing means, such as a cam, displaces one cylinder segment of each pair of cylinder segments relative to the other cylinder segments so that the batt is torn. In the instance of each patent there are pivotal means involving displacing jaws so that operational techniques require extra care in cleaning and maintenance and pivoting parts are easily worn.

Another technique for forming individual panels of loose fibers, which may be rectangular in shape or in other desired shapes, without forming the harsh compressed lines produced by cutting the batt is disclosed in U.S. Pat. No. 3,973,291 assigned to Scott Paper Co. In this patent, the panels are formed individually by air laying the fibers within a pattern of the desired size and shape. As described in the aforementioned patent, the machinery required to produce such individually air laid panels and convey such panels is quite large and cumbersome and relatively complex in its moving parts and operation.

Also in the co-pending, commonly assigned patent application Ser. No. 888,818 filed Mar. 21, 1978, now U.S. Pat. No. 4,216,687, there is disclosed an apparatus which utilizes air jets to shape and partition a loose batt of fibers into individual shaped panels. While the machine disclosed in the above-mentioned patent application is relatively simple in construction and operation, it does require means for generating an air supply and maintaining the air clean which is an added cost in the manufacture of the desired absorbent product.

In a further example, German Pat. No. 1,252,050 to Hesser, a device is shown for separating cardboard sections defined by lines of weakening from a continuous strip of cardboard. The section to be severed from the strip is held between a rubber bar and an underlying roller while the rest of the continuous strip is moved rearwardly by the action of a single, slideably-mounted segment of the underlying roller. In contradistinction thereto, the present invention provides a simple and economical method and apparatus for partitioning and/or shaping a continuously moving batt which is fed between a pair of rolls rotating in opposite directions. The rolls have engaging jaw members such that the batt is partitioned and/or shaped in a manner to provide clean lines with no densification of the batt material.

SUMMARY OF THE INVENTION

The present apparatus for partitioning and/or shaping a batt of loosely compacted short fibers into individual panels of short fibers comprises a pair of rolls disposed adjacent each other with their axes parallel. The rolls are rotatable in opposite directions but at the same peripheral linear speed. The rolls each have at least one jaw member affixed to the roll and extending along the surface of the roll about a portion of the periphery of the roll. When the apparatus is to partition the batt into individual panels, the jaw member is disposed along the surface of the roll parallel to the roll axis, a distance at least equal to the width of the batt being partitioned. When the apparatus is to be used to shape a batt, the jaw member is disposed along the surface of the roll about a portion of the periphery of the roll in the shape or pattern which it is desired to form in the batt. In certain embodiments of the present invention, the rolls may each have at least one jaw member to partition the batt and at least one jaw member to shape the batt.

Each jaw member has a non-resilient means and a resilient means disposed adjacent each other. The non-resilient means is constructed so that the furthest tip of the means projects outwardly from the surface of the roll at least about 0.03 inch. The non-resilient means has a first face forming the furthest tip, the first face being disposed perpendicular to a plane in which the axis of the roll lies. The second face of the non-resilient means forms an angle of 90° or less with the first face at one end thereof and extends from the end at least to the surface of the roll. A third face extends from the opposite end of the first face to the surface of the roll. The resilient means is disposed adjacent the second face of the non-resilient means and has a first face disposed perpendicular to a plane in which the axis of the roll lies. The resilient means also has a second face forming an angle of about 90° or less with the first face at one end thereof and extending from the end to the surface of the roll. A third face of the resilient means extends from the opposite end of the first face to the surface of the roll. The resilient means projects outwardly from the surface of the roll at least about as far as the non-resilient means and extends along the surface of the roll adjacent the non-resilient means. The apparatus includes a means for rotating the rolls in opposite directions so that the jaw members on the oppositely rotating rolls engage each other in a manner such that the non-resilient means of one roll engages the oppositely rotating resilient means of the other roll with the second face of the non-resilient means of one roll passing the second face of the non-resilient means of the other roll with a clearance between the faces of at least 0.01 inch.

The present invention includes a method for partitioning and/or shaping a continuous batt of loosely compacted short fibers into a plurality of individual shaped panels of the fibers. The method includes conveying a batt of loosely compacted short fibers in a direction and gripping the batt along a first path with a resilient means engaging a first surface of the batt and a non-resilient means engaging the second surface of the batt. Substantially immediately thereafter, the batt is gripped along a second path adjacent the first transverse line with a non-resilient means engaging the first surface of the batt and a resilient means engaging the second surface of the batt. Thereafter, the first and second lines are displaced with respect to each other from the plane of the batt and on opposite sides of the plane. Thus the batt is ruptured. The batt is then released to separate the ruptured batt from the remainder of the batt and the lines return to their original plane.

When the first path as described is a transverse line extending the width of the batt and the second path is also a transverse line extending the width of the batt and adjacent the first transverse line, the method of the present invention will separate the batt into individual panels. When the first and second paths are complementary shaped or patterned lines, the method of the present invention will shape the batt into the desired pattern. When both such transverse lines and shaped or patterned lines are used, the method of the present invention will produce individually shaped panels from the batt of fibers.

A feature of the invention is that the panels are partitioned and/or shaped from a continuously moving absorbent batt without compression of the fibers at the severance lines. In addition, the speed of partitioning and/or shaping the absorbent batt is very high and has been shown to reach at least 500 panels or 750 feet per minute. The mechanism of the apparatus of the present invention is quite simple. As a result, it is inexpensive to produce, and easy to operate and maintain. Furthermore, there is little, if any, wear of the parts.

BRIEF DESCRIPTION OF THE DRAWINGS

FIG. 1 is a perspective view of an apparatus embodying the present invention;

FIG. 2 is a front view of one embodiment of apparatus in accordance with the present invention;

FIGS. 3A, 3B and 3C are cross-sectional views taken through the line 3—3 of FIG. 2 and depict step-wise progression of the movement of the rolls;

FIG. 4 is a front view of another embodiment of apparatus of the present invention;

FIG. 5 is an expanded view showing a jaw member of one of the rotatable rolls; and FIG. 6 is a cross-sectional elevational view of a particular embodiment of the apparatus of the present invention.

DETAILED DESCRIPTION OF THE INVENTION

Referring to the drawings, in FIGS. 1 and 2 there is shown the absorbent batt partitioning apparatus 10 of the present invention. In the apparatus, a pair of rolls 12 and 14 are mounted on a frame 25 only a portion of which is shown in the drawings for the sake of clarity. The rolls are mounted adjacent one another with their axes parallel. The upper roll rotates in the direction shown by the arrow and the lower roll rotates in the opposite direction.

The rolls 12 and 14 are provided with jaw members 11 and 13, respectively. The jaw members comprise non-resilient means 16 and 18, and resilient means 26 and 28, respectively. The rolls 12 and 14 are mounted in the frame 25 and are geared for rotation through gears 22 and 24 respectively. The rolls are driven by any suitable means 23 well known in the art.

When rotating, the rolls cooperate to engage the jaw members so that each non-resilient means compresses the opposing resilient means.

As is more clearly shown in FIGS. 3A, 3B and 3C, the batt of loosely compacted short fibers 20 is conveyed in a path to a point of gripping 70 along a first transverse line with the resilient means 28 engaging a first surface of the batt and non-resilient means 16 engaging the second surface of the batt. Immediately thereafter, the batt is gripped along a second transverse line 72 adjacent the first transverse line with a non-resilient means 18 engaging the first surface of the batt and resilient means 26 engaging the second surface of the batt. In FIG. 3B the first and second lines 70 and 72 are displaced with respect to each other from the plane of the batt and on opposite sides of the plane. In FIG. 3C the batt is released to form and partition an individual panel 20A from the batt 20.

The transverse lines 70 and 72 lie immediately before and immediately after the point of partition of the fibrous batt.

Referring to FIG. 4 there is shown another embodiment of apparatus in accordance with the present invention. In this embodiment, the apparatus is used to shape a batt of loose fibers. The apparatus comprises a pair of rolls 30 and 32 mounted for rotation in a frame not shown for the sake of clarity. The rolls are mounted adjacent one another with their axes parallel. The apparatus includes means for rotating the rolls in opposite directions at the same peripheral linear speed. The rotating means has been omitted from the drawings also for the sake of clarity.

The rolls 30 and 32 are provided with jaw members 34, 35, 36, and 37 respectively. In this embodiment the jaw members are mounted about the portion of the periphery of the rolls in a pattern so as to produce the desired shape in the batt to be treated. The jaw members comprise non-resilient means 38 and resilient means 40. When rotating the rolls cooperated to engage the jaw members so that each non-resilient means compresses the opposing resilient means.

FIG. 5 is an enlarged cross-sectional view depicting a typical jaw member in detail. The non-resilient means 50 is provided with a first face 51. The first face is perpendicular to a plane which the axis of the roll containing the jaw member lies. The non-resilient means has a second face 52. The two faces form an angle 53 of not more than 90°, preferably the angle 53 is less than 90° to provide space for clearance of the opposing jaw member. A third face 54 trails tangentially from the first face 51 to the surface of the roll. The resilient means 56 is comprised of rubber or other suitable resilient material and is provided with a first face 57 perpendicular to a plane in which the axis of the roll containing the jaw member lies. A second face 58 is substantially perpendicular to the first face 57 and extends from the first face to the surface of the roll at least as far as the second face of the non-resilient means 50. Between the second face of the resilient means and the second face of the non-resilient means is a space 59. The resilient means also is provided with a third face 60 trailing from the first face 57 to the surface of the roll from the side opposite the second face.

Referring again to FIG. 3B it should be noted that at the point of maximum engagement of jaws 11 and 13 there is a space 19 between the non-resilient means 16 and 18. This space is substantially rectangular in shape and is at least 0.01 inch in width. The space allows for clearance of the jaws one from another without placing pressure on the partitioned edge.

The jaw member is affixed to the roll by any convenient means. In the present instance, a groove was cut in the roll and the jaw member was fastened by means of screws to the roll surface in the groove.

Now referring to FIG. 6 an alternate type of jaw member 82 provided on roll 81 is shown. A non-resilient means 84 is the same as the previously described non-resilient means. The resilient means 86 is provided with a metal or nylon fitting 87 which is activated by a spring 88. Controlling the action of the spring is a shoulder screw or a guide rod 90 the latter of which is housed in channel 94 and moves up and down in the channel.

As the jaw member is engaged with an opposing jaw member the metal or nylon fitting is depressed against the spring. After engagement of the jaw member the fitting 87 is restored by the spring to its original position.

Referring again to FIGS. 1 and 2 the rolls 12 and 14 are spaced slightly apart leaving a space 17. This space should be at least 0.01 inch and is varied according to the thickness of the batt which is being partitioned and/or shaped. In fact the gap between the rolls and the space between the second faces of the non-resilient means when being engaged and the penetration of the first face of the non-resilient means against the first face of the resilient means are all dependent upon the thickness and nature of the batt to be partitioned. For example when preparing an absorbent panel for a disposable diaper an absorbent batt having a width of 12 inches is partitioned into panels having a length of 17½ inches the entire panel weighing approximately 66 grams. During operation of the apparatus while severing the absorbent batt the gap between the rolls is ⅛ inch and the penetration of the first face of the non-resilient means against the first face of the resilient means is 0.15 inch below the surface of the opposing roll. The space between the second faces of the non-resilient means is 0.03 inch.

The projection of the non-resilient means to the furthest tip from the surface of the roll is at least 0.12 inch. Preferably the projection is at least 0.15 inch. As the thickness of the batt or web which it is desired be partitioned or shaped increases, it is not necessarily required that the projection of the furthest face of the non-resilient means be altered, but as the batt or web increases in thickness, the gap between the surface of the rolls should be widened. The gap between the rolls should at all times be less than the thickness of the batt which is being treated.

Batts made from short cellulosic fibers are particularly suitable for partitioning and/or shaping by the apparatus and method of the present invention. An example of a typical short cellulosic fibrous batt is the absorbent panel found in disposable diapers. These particular fibrous batts are obtained by the grinding or comminution of compacted wood pulp fibers or cotton linters. The compacted cellulosic material is at a moisture content of 5–10% by weight before being subjected to a grinding operation so that the fibers produced by grinding have sufficient moisture to have the capability of developing weak interfiber hydrogen bonds which give some coherence to the body of the absorbent batt. The batts are initially formed by air blowing the slightly moist cellulosic fibers onto a support and then subjecting the airblown fibers to heavy compression. The small amount of moisture which is present is uniformly distributed throughout the airblown fibers and after compression give some integrity to the body of the batt. The short fibers used in making the batt are generally entirely fibers of wood pulp or cotton linters. However, other cellulosic fibers may be used as well as blends of cellulosic fibers with other fibers such as silk, wool, nylon, rayon or cellulose acetate.

The term "short fibers" as used herein refers to fibers less than about ½ inch in length. Batts or webs formed from fibers of a longer length can be satisfactorily partitioned and/or shaped using the proper adjustments of the projection of the furthest face of the non-resilient means and the gap between the rolls.

In partitioning batts or webs according to the present invention virtually any length panel may be formed. Also in shaping batts according to the present invention numerous types of shapes may be produced; such as hourglass, rectangular, trapezoidal, or even free formed shapes if desired.

The rolls can be made of any solid material upon which the jaw members can be affixed. For example, hard rubber, metal, wood or the like. Suitable materials for making the non-resilient means include metal, wood, plastic or the like. The resilient means is preferably made of a material such as rubber, which can be compressed and upon release returns to its original form. The resilient means as depicted in FIG. 6 may also be constructed in such a way that a hard material can be used for the exterior of the resilient means.

The jaw member is preferably constructed in such a way that the angle formed by the second face and first face of the non-resilient means is approximately 80° or less. The first face of both the non-resilient and the resilient means should be of sufficient width from the leading edge to permit gripping of the batt when it first encounters the respective faces. The third face of the resilient means or the non-resilient means can simply trail from the first face back to the surface of the roll. However, alternatively, the third face may create a sharp angle from the first face back to the surface of the roll.

In a specific embodiment of the present invention, a disposable diaper panel is formed by partitioning an absorbent batt made from loosely compacted short cellulose fibers. The batt is initially formed by airblowing the slightly moist cellulosic fibers onto a support at a total weight of 2 to 10 oz/yd$^2$ and then subjecting the airblown fibers to heavy compression. The resulting batt is approximately 10½ inches wide and proceeds on a conveyor line to the panel partitioning apparatus of the present invention. The batt is partitioned to a length of 17½ inches and weighs approximately 66 grams. The gap between the rolls is 0.12 inch and the protrusion of the first face of the jaw member from the surface of the roll to which it is affixed is 0.21 inch.

It may be desirable for the absorbent panel, particularly when it is to be used in a disposable diaper, to include a thin skin of lightly hydrogen-bonded wood pulp fibers on one surface of the batt to improve specific absorbent characteristics of the batt. Such a skin is more fully described in U.S. Pat. Nos. 3,017,304 and 3,612,055.

Whether or not a skin is present, the partitioning and/or shaping afforded by the apparatus and method of the present invention eliminates formation of any densified layer or thickening at the edge of the panels.

The foregoing description and drawings are illustrative but are not to be taken as limiting. Other variations and modifications are possible without departing from the spirit and scope of the present invention.

I claim:

1. A method for shaping a web comprising: conveying a web in a direction, gripping the web along a first path with a resilient means engaging a first surface of the web and non-resilient means engaging the second surface of the web, substantially immediately thereafter gripping the web along a second path immediately adjacent said first path with a non-resilient means engaging said first surface of the web and resilient means engaging the second surface of the web, substantially immediately thereafter displacing said first path and second path with respect to each other from the plane of the web and on opposite sides of said plane, and releasing the web to provide a shaped web.

2. A method for shaping a batt of loosely compacted short fibers comprising: conveying a batt of loosely compacted short fibers in a direction, gripping the batt along a first path with a resilient means engaging a first surface of the batt and non-resilient means engaging the second surface of the batt, substantially immediately thereafter gripping the batt along a second path immediately adjacent said first path with a non-resilient means engaging said first surface of the batt and resilient means engaging the second surface of the batt, substantially immediately thereafter displacing said first and second path with respect to each other from the plane of the batt and on opposite sides of said plane, and releasing the batt to provide a shaped batt.

3. A method for partitioning a continuous web into a plurality of individual panels of web material comprising: conveying a web in a direction, gripping the web along a first transverse line with a resilient means engaging a first surface of the web and non-resilient means engaging the second surface of the web, substantially immediately thereafter gripping the web along a second transverse line immediately adjacent said first transverse line with a non-resilient means engaging said first surface of the web and resilient means engaging the second surface of the web, substantially immediately thereafter displacing said first and second lines with respect to each other from the plane of the web and on opposite sides of said plane, and releasing the web to form and partition an individual panel from the web.

4. A method for partitioning a continuous batt of loosely compacted short fibers into a plurality of individual panels of said fibers comprising: conveying a batt of loosely compacted short fibers in a direction, gripping the batt along a first transverse line with a resilient means engaging a first surface of the batt and non-resilient means engaging the second surface of the batt, substantially immediately thereafter gripping the batt along a second transverse line immediately adjacent said first transverse line with a non-resilient means engaging said first surface of the batt and resilient means engaging the second surface of the batt, substantially immediately thereafter displacing said first and second lines with respect to each other from the plane of the batt and on opposite sides of said plane, and releasing the batt to form and partition an individual panel from the batt.

5. Apparatus for shaping a web of fibers comprising: a pair of rolls disposed adjacent each other with their axes parallel, said rolls each having at least one jaw member affixed to the roll and extending about a portion of the periphery of the roll, each jaw member comprising a non-resilient means and a resilient means disposed adjacent each other, said non-resilient means being constructed with a furthest tip of said means projecting outwardly from the surface of the roll at least about 0.1 inch; the non-resilient means having a first face forming said furthest tip, said first face disposed perpendicular to a plane in which the axis of the roll lies, a second face forming an angle of 90° or less with said first face at oned end thereof and extending from said end at least to the surface of the roll, and a third face extending from the opposite end of said first face to the surface of the roll; the resilient means disposed adjacent the second face of the non-resilient means, said resilient means having a first face disposed perpendicular to a plane in which the axis of the roll lies, a second face forming an angle of about 90° or less with said first face at one end thereof and extending from said end to the surface of the roll, and a third face extending from the opposite end of said first face to the surface of the roll, said resilient means projecting outwardly from the surface of the roll at least about as far as said non-resilient means and extending along the surface of the roll at least as far as said non-resilient means, and means for rotating the rolls in opposite directions so that jaw members on the oppositely rotating rolls engage each other in a manner that the non-resilient means of one roll engages the oppositely rotating resilient means of the other roll with the second face of the non-resilient means of one roll passing the second face of the non-resilient means of the other roll with a clearance between the faces of at least 0.03 inch.

6. Apparatus for shaping a batt of loosely compacted short fibers comprising: a pair of rolls disposed adjacent each other with their axes parallel, said rolls each having at least one jaw member affixed to the roll and extending about a portion of the periphery of the roll, each jaw member comprising a non-resilient means and a resilient means disposed adjacent each other, said non-resilient means being constructed with a furthest tip of said means projecting outwardly from the surface of the roll at least about 0.1 inch; the non-resilient means having a first face forming said furthest tip, said first face disposed perpendicular to a plane in which the axis of the roll lies, a second face forming an angle of 90° or less with said first face at one end thereof and extending from said end at least to the surface of the roll, and a third face extending from the opposite end of said first face to the surface of the roll; the resilient means disposed adjacent the second face of the non-resilient means, said resilient means having a first face disposed perpendicular to a plane in which the axis of the roll lies, a second face forming an angle of about 90° or less with said first face at one end thereof and extending from said end to the surface of the roll, and a third face extending from the opposite end of said first face to the surface of the roll, said resilient means projecting outwardly from the surface of the roll at least about as far as said non-resilient means and extending along the surface of the roll at least as far as said non-resilient means, and means for rotating the rolls in opposite directions so that jaw members on the oppositely rotating rolls engage each other in a manner that the non-resilient means of one roll engages the oppositely rotating resilient means of the other roll with the second face of the non-resilient means of one roll passing the second face of the non-resilient means of the other roll with a clearance between the faces of at least 0.03 inch.

7. Apparatus as set forth in claim 6 wherein there is a space of at least 0.03 inch between the surfaces of the two oppositely rotating rolls.

8. Apparatus as set forth in claim 6 wherein there are two jaw members affixed to each roll and disposed about a portion of the periphery of the roll such as to shape the longitudinal edges of the batt in a complementary manner as the batt passes between the rolls.

9. Apparatus as set forth in claim 8 wherein there is a space of at least 0.03 inch between the surfaces of the two oppositely rotating rolls.

10. Apparatus as set forth in claim 8 wherein there is a space of at least 0.1 inch between the surfaces of the two oppositely rotating rolls.

11. Apparatus as set forth in claim 10 wherein the furthest tip of each jaw member extends approximately 0.2 inch from the surface of the roll.

12. Apparatus as set forth in claim 6 wherein the resilient means are rubber.

13. Apparatus as set forth in claim 6 wherein the resilient means are spring loaded metal means.

14. Apparatus for partitioning a batt of loosely compacted short fibers comprising: a pair of rolls disposed adjacent each other with their axes parallel, said rolls each having at least one jaw member affixed to the roll and extending along the surface of the roll parallel to the roll axis a distance at least equal to the width of the batt being partitioned; each jaw member comprising a non-resilient means and a resilient means disposed adjacent each other, said non-resilient means being constructed with the furthest tip of said means projecting outwardly from the surface of the roll at least about 0.1 inch; the non-resilient means having a first face forming said furthest tip, said first face disposed perpendicular to a plane in which the axis of the roll lies, a second face forming an angle of 90° or less with said first face at one end thereof an extending from said end at least to the surface of the roll, and a third face extending from the opposite end of said first face to the surface of the roll; the resilient means disposed adjacent the second face of the non-resilient means, said resilient means having a first face disposed perpendicular to a plane in which the axis of the roll lies; a second face forming an angle of about 90° with said first face at one end thereof and extending from said end to the surface of the roll, and a third face extending from the opposite end of said first face to the surface of the roll, said resilient means projecting outwardly from the surface of the roll at least about as far as said non-resilient means and extending along the surface of the roll parallel to the roll axis at least as far as said non-resilient means, and means for rotating the rolls in opposite directions so that jaw members on the oppositely rotating rolls engage each other in a manner that the non-resilient means of one roll engages the oppositely rotating resilient means of the other roll with the second face of the non-resilient means of one roll passing the second face of the non-resilient means of the other roll with a clearance between the faces of at least 0.03 inch.

15. Apparatus as set forth in claim 14 wherein there is a space of at least 0.03 inch between the surfaces of the two oppositely rotating rolls.

16. Apparatus as set forth in claim 15 wherein the space is approximately 0.1 inch.

17. Apparatus as set forth in claim 16 wherein the furthest tip of each jaw member extends approximately 0.2 inch from the surface of the roll.

18. Apparatus as set forth in claim 14 wherein the resilient means are resilient material or non-resilient material which are spring loaded.

19. Apparatus as set forth in claim 18 wherein the resilient material is rubber.

20. Apparatus as set forth in claim 18 wherein the resilient means are spring loaded metal means.

21. Apparatus for shaping and partitioning a batt of loosely compacted short fibers comprising: a pair of rolls disposed adjacent each other with their axes parallel, said rolls each having at least two jaw members affixed to the roll, one jaw member extending about a portion of the periphery of the roll and the other jaw member extending along the surface of the roll parallel to the roll axis a distance at least equal to the width of the batt being partitioned; each jaw member comprising a non-resilient means and a resilient means disposed adjacent each other, said non-resilient means being constructed with the furthest tip of said means projecting outwardly from the surface of the roll at least about 0.01 inch; the non-resilient means having a first face forming said furthest tip, said first face disposed perpendicular to a plane in which the axis of the roll lies, a second face forming an angle of 90° or less with said first face at one end thereof and extending from said end at least to the surface of the roll, and a third face extending from the opposite end of said first face to the surface of the roll; the resilient means disposed adjacent the second face of the non-resilient means, said resilient means having a first face disposed perpendicular to a plane in which the axis of the roll lies; a second face forming an angle of about 90° with said first face at one end thereof and extending from said end to the surface of the roll, and a third face extending from the opposite end of said first face to the surface of the roll, said resilient means projecting outwardly from the surface of the roll at least about as far as said non-resilient means and extending along the surface of the roll at least as far as said non-resilient means, and means for rotating the rolls in opposite directions so that jaw members on the oppositely rotating rolls engage each other in a manner that the nonresilient means of one roll engages the oppositely rotating resilient means of the other roll with the second face of the non-resilient means of one roll passing the second face of the non-resilient means of the other roll with a clearance between the faces of at least 0.03 inch.

22. Apparatus as set forth in claim 21 wherein the resilient means are resilient material or non-resilient material which are spring loaded.

23. Apparatus as set forth in claim 22 wherein the resilient material is rubber.

24. Apparatus as set forth in claim 22 wherein the resilient means are spring loaded metal means.

25. Apparatus as set forth in claim 21 wherein each roll has three jaw members, two of said jaw members being disposed about a portion of the periphery of the roll such as to shape the longitudinal edges of the batt and the third jaw member extending along the surface of the roll parallel to the roll axis a distance at least equal to the width of the batt to partition the batt into individually substantially hourglass shaped panels.

26. Apparatus as set forth in claim 25 wherein there is a space of at least 0.03 inch between the surfaces of the two oppositely rotating rolls.

27. Apparatus as set forth in claim 26 wherein the space is approximately 0.1 inch.

28. Apparatus as set forth in claim 25 wherein the furthest tip of each jaw member extends approximately 0.2 inch from the surface of the roll.

29. Apparatus as set forth in claim 25 wherein the resilient means are resilient material or non-resilient material which are spring loaded.

30. Apparatus as set forth in claim 29 wherein the resilient means is rubber.

31. Apparatus as set forth in claim 29 wherein the resilient means are spring loaded metal means.

* * * * *